(12) United States Patent
Mollison

(10) Patent No.: US 6,329,386 B1
(45) Date of Patent: Dec. 11, 2001

(54) TETRAZOLE-CONTAINING RAPAMYCIN ANALOGS WITH SHORTENED HALF-LIVES

(75) Inventor: Karl W. Mollison, Arlington Heights, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/433,001

(22) Filed: Nov. 2, 1999

Related U.S. Application Data

(62) Division of application No. 09/159,945, filed on Sep. 24, 1998, now Pat. No. 6,015,815.
(60) Provisional application No. 60/060,105, filed on Sep. 26, 1997, now abandoned.

(51) Int. Cl.[7] .................................................... A61K 31/44
(52) U.S. Cl. ............................................................ 514/291
(58) Field of Search ............................................. 514/291

(56) References Cited

U.S. PATENT DOCUMENTS

| | | |
|---|---|---|
| 3,929,992 | 12/1975 | Sehgal et al. . |
| 3,993,749 | 11/1976 | Sehgal et al. . |
| 4,316,885 | 2/1982 | Rakhit . |
| 4,401,653 | 8/1983 | Eng . |
| 4,650,803 | 3/1987 | Stella et al. . |
| 4,885,171 | 12/1989 | Surendra et al. . |
| 5,023,262 | 6/1991 | Caufield et al. . |
| 5,120,725 | 6/1992 | Kao et al. . |
| 5,120,727 | 6/1992 | Kao et al. . |
| 5,120,842 | 6/1992 | Failli et al. . |
| 5,177,203 | 1/1993 | Failli et al. . |
| 5,457,111 | 10/1995 | Luly et al. . |
| 5,527,907 | 6/1996 | Or et al. . |

FOREIGN PATENT DOCUMENTS

| | | |
|---|---|---|
| 0184162 | 6/1986 | (EP) . |
| 0467606 | 1/1992 | (EP) . |
| 9205179 | 4/1992 | (WO) . |
| 9514023 | 5/1995 | (WO) . |
| 9809970 | 3/1998 | (WO) . |
| 9809972 | 3/1998 | (WO) . |

OTHER PUBLICATIONS

Prescott, ed., Methods in Cell Biology, vol. XIV, Academic Press, New York, NY (1976), p. 33–71.

C. Vezina et al., "Rapamycin (AY–22, 989), A New Antifungal Antibiotic I", Journal of Antibiotics, vol. 28, (1975), pp. 721–726.

S. N. Sehgal et al., "Rapamycin (AY–22, 989), A New Antifungal Antibiotic II", Journal of Antibiotics, vol. 28, (1975), pp. 727–732.

N. L. Pavia et al., "Incorporation into Rapamycin", Journal of Natural Products–Lloydia, vol. 54, No. 1, (1991), pp. 167–177.

E. J. Brown et al., "A Mammalian Protein Targeted by G1–arresting Rapamycin–Receptor Complex", Nature, vol. 369, (1994), pp. 756–758.

C. Hayward et al., "Total Synthesis of Rapamycin vis a Novel Titanium–Mediated Aldol Macrocyclization Reaction", Journal of the American Chemical Society, vol. 115 (1993), pp. 9345–9346.

Romo "Total Synthesis of (—) —Rapamycin Using an Evans–Tishchenko Fragment Coupling", Journal of the American Chemical Society, vol. 115, (1993), pp. 7906–7907.

K. C. Nicolau et al., "Total Synthesis of Rapamycin", Journal of the American Chemical Society, vol. 115, (1993), pp. 4419–4420.

H. Fretz et al., "Rapamycin and FK506 Binding Proteins (Immunophilins)", Journal of the American Chemical Society, vol. 113 (1991), pp. 1409–1411.

F.J. Dumont et al., "The Immunosuppressive Macrolides FK–506 and Rapamycin Act as Reciprocal Antagonists in Murine T Cells", Journal of Immunology, vol. 144, (1990), pp. 1418–1424.

M. Shichiri et al., "Endothelin–1 is an Autocrine/Paracrine Growth Factor for Human Cancer Cell Lines", Journal of Clinical Investigation, vol. 87, (1991), pp. 1867–1871.

(List continued on next page.)

Primary Examiner—Rebecca Cook
(74) Attorney, Agent, or Firm—Dugal S. Sickert; Robert A. Miller

(57) ABSTRACT

A compound having the formula

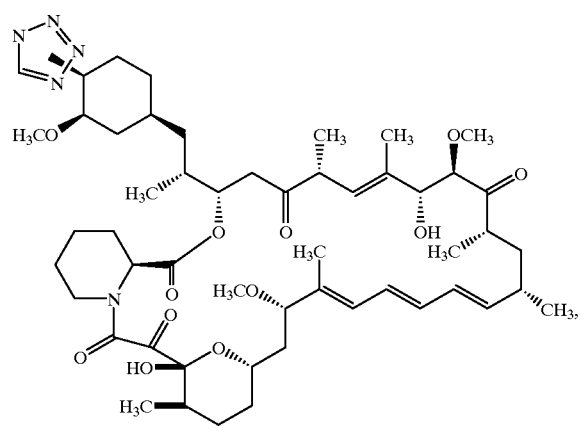

or a pharmaceutically acceptable salt or prodrug thereof, is an immunomodulatory agent and is useful in the treatment of restenosis and immune and autoimmune diseases. Also disclosed are cancer-, fungal growth-, restenosis-, post-transplant tissue rejection- and immune- and autoimmune disease-inhibiting compositions and a method of inhibiting cancer, fungal growth, restenosois, post-transplant tissue rejection, and immune and autoimmune disease in a mammal.

21 Claims, 1 Drawing Sheet

OTHER PUBLICATIONS

B.E. Bierer et al., "The Effect of the Immunosuppressant FK–506 on Alternate Pathways of T Cell Activation", European Journal of Immunology, vol. 21, (1991), pp. 439–445.

S.N. Sehgal et al., "Demethoxyrapanycin (AY–24, 688), A New Antofungal Antibiotic", Journal of Antibiotics, vol. 36, No. 4, (1983), pp. 351–354.

D.M. Sabatini et al., "RAFT1: A Mammalian Protein that Binds to FKBP12 in a Rapamycin–Dependent Fashion and is Homologous to Yeast TORs", Cell, vol. 78, (1994), pp. 35–43.

R. Martel et al., "Inhibition of the Immune Response by Rapamycin, a New Antifungal Antibiotic", Canadian Journal of Physiology and Pharmacology, vol. 55, (1977), pp. 48–51.

S. Yamagishi et al., "Endothelin 1 Mediates Endothelial Cell–Dependent Proliferation of Vascular Pericytes", Biochemical and Biophyscial Research Communications, vol. 191, (1993), pp. 840–846.

T. Kino et al., "Effect of FK–506 on Human Mixed Lymphocyte Reaction in Vitro", Transplantation proceedings, vol. XIX, No. 5 sup. 6, (1987), pp. 36–39.

T.E. Bunchman et al., "Smooth Muscle Cell Proliferation by Conditioned Media from Cyclosporine–Treated Endothelial Cells: A Role of Endothelin", Transplantation Proceedings, vol. 23, No. 1, (1991), pp. 967–968.

R. Morris et al., "Identification of a New Pharmacologic Action for an Old Compound", Medical Science Research, vol. 17, (1989), pp. 877–879.

M.J. Strauch, FASEB, 3 (3): 3411 (1989).

H. A. Baker et al., "Rapamycin (AY–22, 989), A New Antifungal Antibiotic III", Journal of Antibiotics, vol. 31, (1978), pp. 539–545.

J. J. Siekierka et al., "A Cytosolic Binding Protein for the Immunosuppressant FK506 has Peptidyl–prolyl Isomerase Activity but is Distinct from Cyclophilin", Nature, vol. 341, (1989), pp. 755–757.

M. W. Harding et al., "A Receptor for the Immunosuppressant FK506 is a cistrans Peptidyl–prolyl Isomerase", Nature, vol. 341 (1989), pp. 758–760.

R. E. Morris, "Rapamycins: Antifungal, Antitumor, Antiproliferative, and Immunospressive Macrolides", Transplantation Reviews, vol. 6., No. 1, (1992), pp. 39–87.

TETRAZOLE-CONTAINING RAPAMYCIN ANALOGS WITH SHORTENED HALF-LIVES

CROSS REFERENCE TO RELATED APPLICATIONS

This application is a division of application Ser. No. 09/159,945 filed Sep. 4, 1998 now U.S. Pat. No. 6,015,815 which in turn is a continuation-in-part of U.S. Provisional application Ser. No. 60/060,105 filed Sep. 26, 1997, and now abandoned.

TECHNICAL FIELD

The present invention relates to novel chemical compounds having immunomodulatory activity and synthetic intermediates useful for the preparation of the novel compounds, and in particular to macrolide immunomodulators. More particularly, the invention relates to semisynthetic analogs of rapamycin, means for their preparation, pharmaceutical compositions containing such compounds, and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al., in European Patent Application No. 184,162, published Jun. 11, 1986, disclose a number of macrocyclic compounds isolated from the genus Streptomyces, including the immunosuppressant FK-506, a 23-membered macrocyclic lactone, which was isolated from a strain of S. tsukubaensis.

Other related natural products, such as FR-900520 and FR-900523, which differ from FK-506 in their alkyl substituent at C-21, have been isolated from S. hygroscopicus yakushimnaensis. Another analog, FR-900525, produced by S. tsukubaensis, differs from FK-506 in the replacement of a pipecolic acid moiety with a proline group. Unsatisfactory side-effects associated with cyclosporine and FK-506 such as nephrotoxicity, have led to a continued search for immunosuppressant compounds having improved efficacy and safety, including an immunosupressive agent which is effective topically, but ineffective systemically (U.S. Pat. No. 5,457,111).

Rapamycin is a macrocyclic triene antibiotic produced by *Streptomyces hygroscopicus*, which was found to have antifungal activity, particularly against *Candida albicans*, both in vitro and in vivo (C. Vezina et al., *J. Antibiot.* 1975, 28, 721; S. N. Sehgal et al., *J. Antibiot.* 1975,28, 727; H. A. Baker et al., *J. Antibiot.* 1978, 31, 539; U.S. Pat. No. 3,929,992; and U.S. Pat. No. 3,993,749).

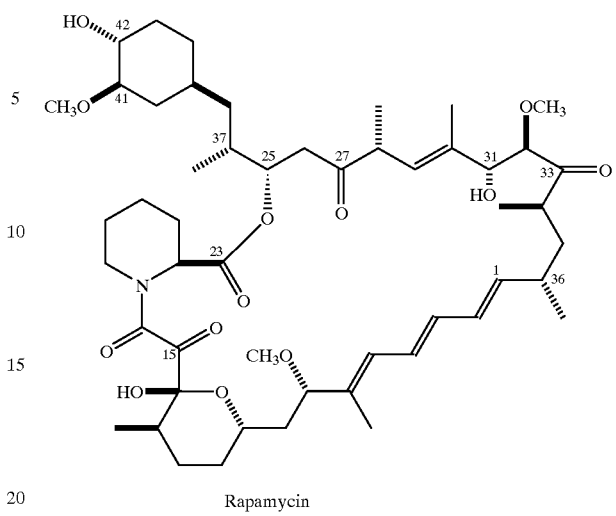

Rapamycin

Rapamycin alone (U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et al., *Can. J. Physiol. Pharmacol.*, 1977, 55, 48).

The immunosuppressive effects of rapamycin have also been disclosed in *FASEB*, 1989, 3, 3411 as has its ability to prolong survival time of organ grafts in histoincompatible rodents (R. Morris, *Med. Sci. Res.*, 1989, 17, 877). The ability of rapamycin to inhibit T-cell activation was disclosed by M. Strauch (*FASEB*, 1989, 3, 3411). These and other biological effects of rapamycin are reviewed in *Transplantation Reviews*, 1992, 6, 39–87.

Mono-ester and di-ester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650, 803).

Fermentation and purification of rapamycin and 30-demethoxy rapamycin have been described in the literature (C. Vezina et al. *J. Antibiot.* (Tokyo), 1975, 28 (10), 721; S. N. Sehgal et al., *J. Antibiot.* (Tokyo), 1975, 28(10), 727; 1983, 36(4), 351; N. L. Pavia et al., *J. Natural Products*, 1991, 54(1), 167–177).

Numerous chemical modifications of rapamycin have been attempted. These include the preparation of mono- and di-ester derivatives of rapamycin (WO 92/05179), 27-oximes of rapamycin (EPO 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120, 842); and arylsulfonates and sulfamates (U.S. Pat. No. 5,177,203). Rapamycin was recently synthesized in its naturally occuring enantiomeric form (K. C. Nicolaou et al., *J. Am. Chem. Soc.*, 1993, 115, 4419–4420; S. L. Schreiber, *J. Am. Chem. Soc.*, 1993, 115, 7906–7907; S. J. Danishefsky, *J. Am. Chem. Soc.*, 1993, 115, 9345–9346.

It has been known that rapamycin, like FK-506, binds to FKBP-12 (Siekierka, J. J.; Hung, S. H. Y.; Poe, M.; Lin, C. S.; Sigal, N. H. *Nature*, 1989,341, 755–757; Harding, M. W.; Galat, A.; Uehling, D. E.; Schreiber, S. L. *Nature* 1989, 341, 758–760; Dumont, F. J.; Melino, M. R.; Staruch, M. J.; Koprak, S. L.; Fischer, P. A.; Sigal, N. H. *J. Immunol.* 1990, 144, 1418–1424; Bierer, B. E.; Schreiber, S. L.; Burakoff, S. J. *Eur. J. Immunol.* 1991, 21, 439–445; Fretz, H.; Albers, M. W.; Galat, A.; Standaert, R. F.; Lane, W. S.; Burakoff, S. J.; Bierer, B. E.; Schreiber, S. L. *J. Am. Chem. Soc.* 1991, 113, 1409–1411). Recently it has been discovered that the rapamycin/FKBP-12 complex binds to yet another protein, which is distinct from calcineurin, the protein that the FK-506/FKBP-12 complex inhibits (Brown, E. J.; Albers, M. W.; Shin, T. B.; Ichikawa, K.; Keith, C. T.; Lane, W. S.; Schreiber, S. L. *Nature* 1994,369, 756–758; Sabatini, D. M.; Erdjument-Bromage, H.; Lui, M.; Tempest, P.; Snyder, S. H. *Cell*, 1994, 78, 35–43).

Although some of these modified compounds exhibit immunosuppressive activity, the need remains for macrocyclic immunosuppressants which do not have the serious side effects frequently associated with immunosuppressant therapy due, in part, to the extended half lives of the immunosupressants. Accordingly, one object of this invention is to provide novel semisynthetic macrolides which possess the desired immunomodulatory activity but which may be found to minimize unwanted side effects due to their shortened half-life.

SUMMARY OF THE INVENTION

Figure 1:
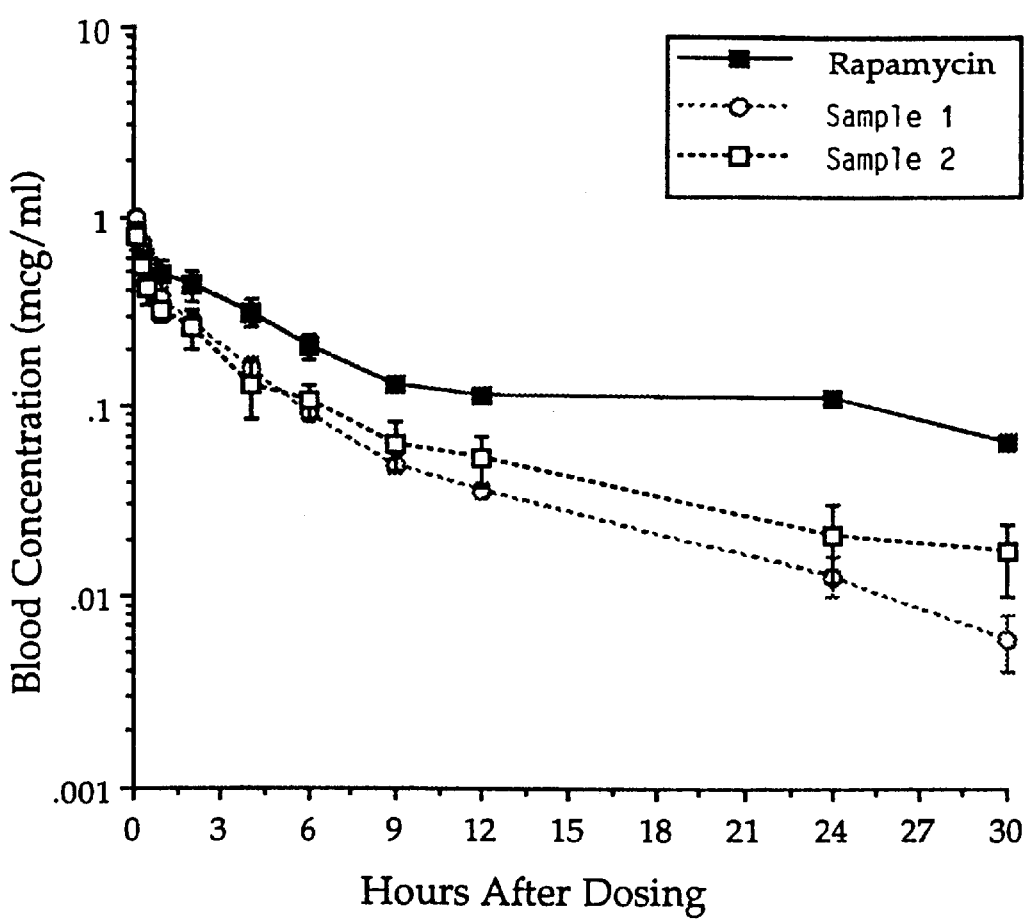
FIG. 1 shows blood concentrations +SEM (n=3) of tetrazole-containing rapamycin analogs dosed in monkey.

In one aspect of the present invention are disclosed compounds represented by the structural formula:

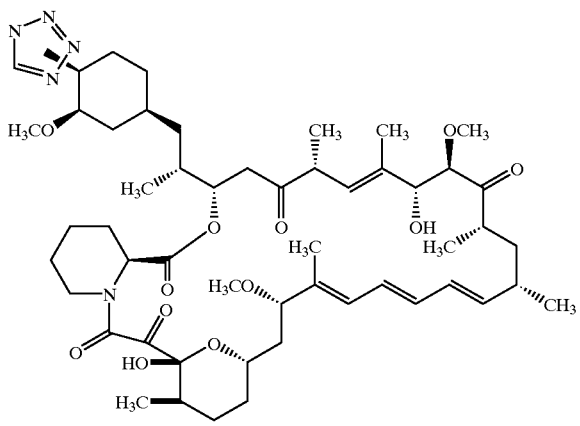

or a pharmaceutically acceptable salt or prodrug thereof.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, at least one of the above compounds.

Yet another object of the invention is to provide a method of treating a variety of disease states, including restenosis, post-transplant tissue rejection, immune and autoimmune dysfunction, fungal growth, and cancer.

DETAILED DESCRIPTION OF THE INVENTION

Definition of Terms

The term "prodrug," as used herein, refers to compounds which are rapidly transformed in vivo to the parent compound of the above formula, for example, by hydrolysis in blood. A thorough discussion is provided in T. Higuchi and V. Stella, "Prodrugs as Novel Delivery Systems," Vol. 14 of the A.C.S. Symposium Series, and in Edward B. Roche, ed., "Bioreversible Carriers in Drug Design," American Pharmaceutical Association and Pergamon Press, 1987, both of which are hereby incorporated by reference.

The term "pharmaceutically acceptable prodrugs," as used herein, refers to those prodrugs of the compounds of the present invention which are, within the scope of sound medical judgement, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention. Particularly preferred pharmaceutically acceptable prodrugs of this invention are prodrug esters of the C-31 hydroxyl group of compounds of this invention.

The term "prodrug esters," as used herein, refers to any of several ester-forming groups that are hydrolyzed under physiological conditions. Examples of prodrug ester groups include acetyl, ethanoyl, pivaloyl, pivaloyloxymethyl, acetoxymethyl, phthalidyl, methoxymetiyl, indanyl, and the like, as well as ester groups derived from the coupling of naturally or unnaturally-occuring amino acids to the C-31 hydroxyl group of compounds of this invention.

Embodiments

In one embodiment of the invention is a compound of formula

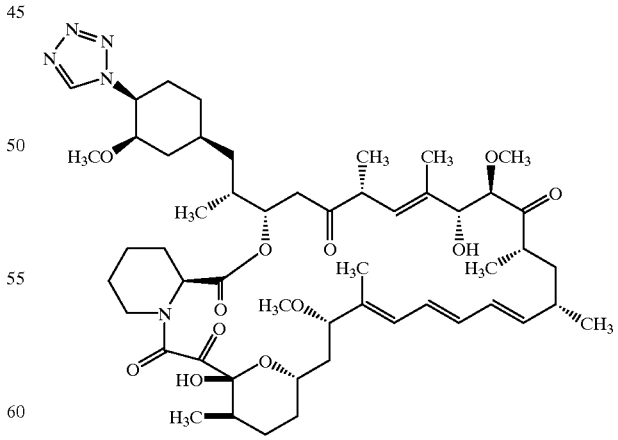

In another embodiment of the invention is a compound of formula

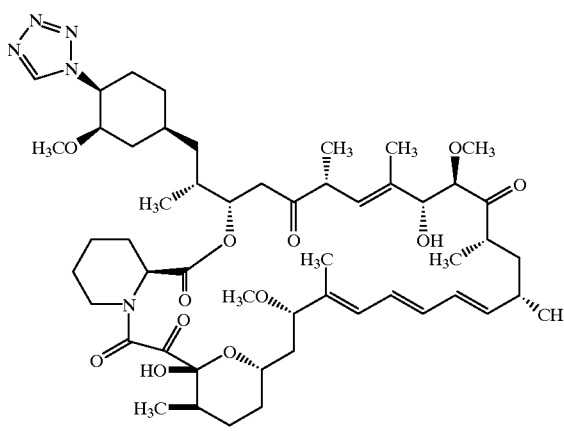

Preparation of Compounds of this Invention

The compounds and processes of the present invention will be better understood in connection with the following synthetic schemes which illustrate the methods by which the compounds of the invention may be prepared.

The compounds of this invention may be prepared by a variety of synthetic routes. A representative procedure is shown in Scheme 1.

Scheme 1

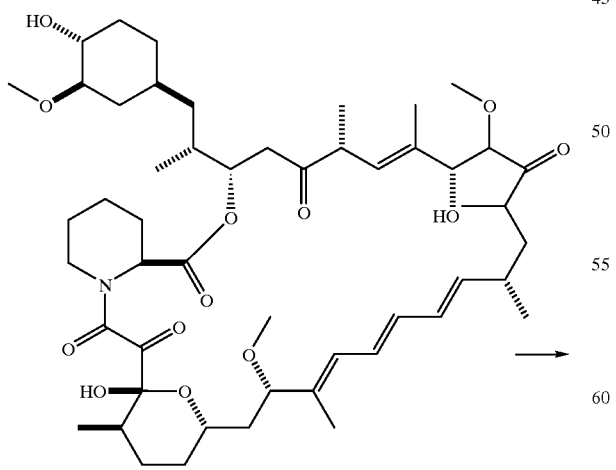

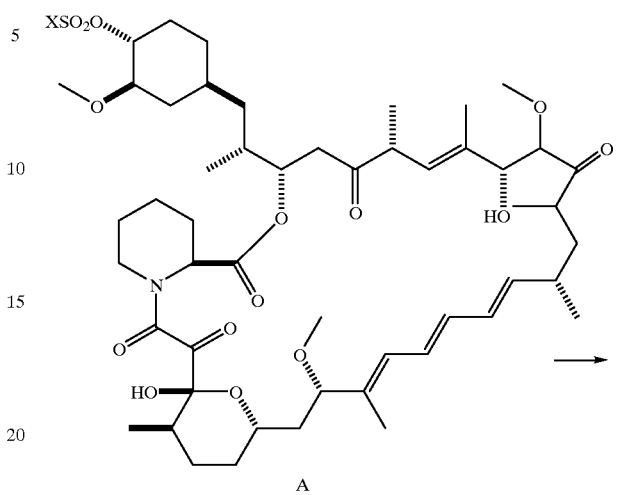

X = F, CF$_3$

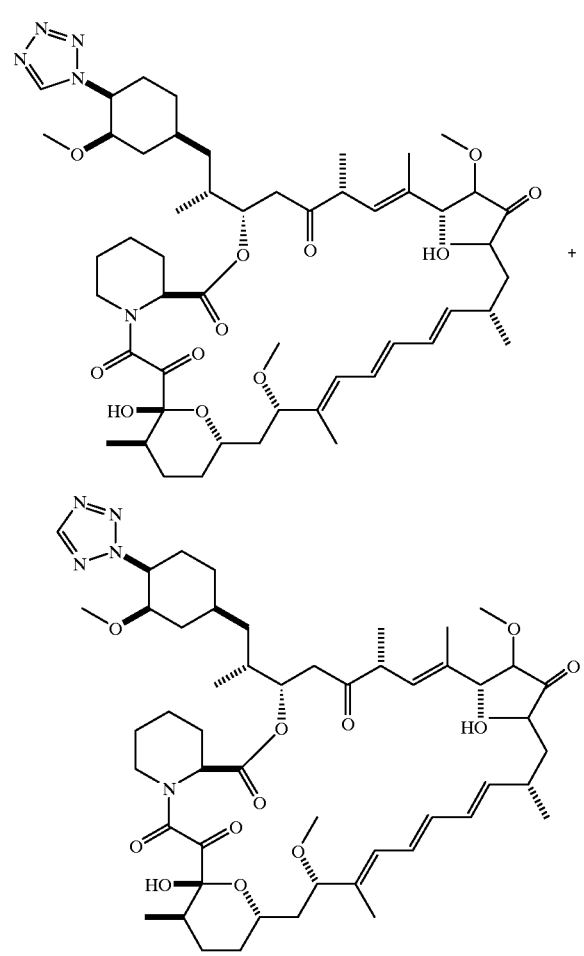

epidermic mixture (B/C)

As shown in Scheme 1, conversion of the C-42 hydroxyl of rapamycin to a trifluoromethanesulfonate or fluorosulfonate leaving group provided A. Displacement of the leaving group with tetrazole in the presence of a hindered, non-nucleophilic base, such as 2,6-lutidine, or, preferably, diisopropylethyl amine provided epimers B and C, which were separated and purified by flash column chromatography.

Synthetic Methods

The foregoing may be better understood by reference to the following examples which illustrate the methods by which the compounds of the invention may be prepared and are not intended to limit the scope of the invention as defined in the appended claims.

EXAMPLE 1

42-Epi-(tetrazolyl)-rapamycin (less polar isomer)

Example 1A

A solution of rapamycin (100 mg, 0.11 mmol) in dichloromethane (0.6 mL) at −78° C. under a nitrogen atmosphere was treated sequentially with 2,6-lutidine (53 uL, 0.46 mmol, 4.3 eq.) and trifluoromethanesulfonic anhydride (37 uL, 0.22 mmol), and stirred thereafter for 15 minutes, warmed to room temperature and eluted through a pad of silica gel (6 mL) with diethyl ether. Fractions containing the triflate were pooled and concentrated to provide the designated compound as an amber foam.

Example 1B

42-Epi-(tetrazolyl)-rapamycin (less polar isomer)

A solution of Example 1A in isopropyl acetate (0.3 mL) was treated sequentially with diisopropylethylamine (87 μL, 0.5 mmol) and 1H-tetrazole (35 mg, 0.5 mmol), and thereafter stirred for 18 hours. This mixture was partitioned between water (10 mL) and ether (10 mL). The organics were washed with brine (10 mL) and dried ($Na_2SO_4$). Concentration of the organics provided a sticky yellow solid which was purified by chromatography on silica gel (3.5 g, 70–230 mesh) eluting with hexane (10 mL), hexane:ether (4:1(10 mL), 3:1(10 mL), 2:1(10 mL), 1:1(10 mL)), ether (30 mL), hexane:acetone (1:1(30 mL)). One of the isomers was collected in the ether fractions. MS (ESI) m/e 966 (M)⁻:

EXAMPLE 2

42-Epi-(tetrazolyl)-rapamycin (more polar isomer)

Example 2A

42-Epi-(tetrazolyl)-rapamycin (more polar isomer)

Collection of the slower moving band from the chromatography column using the hexane:acetone (1:1) mobile phase in Example 1B provided the designated compound. MS (ESI) m/e 966 (M)⁻.

In vitro Assay of Biological Activity

The immunosuppressant activity of the compounds of the present invention was compared to rapamycin and two rapamycin analogs: 40-epi-N-[2'-pyridone]-rapamycin and 40-epi-N-[4'-pyridone]-rapamycin, both disclosed in U.S. Pat. No. 5,527,907. The activity was determined using the human mixed lymphocyte reaction (MLR) assay described by Kino, T. et al. in *Transplantation Proceedings*, XIX(5):36–39, Suppl. 6 (1987). The results of the assay demonstrate that the compounds of the invention are effective immunomodulators at nanomolar concentrations, as shown in Table 1.

TABLE 1

| Example | Human MLR $IC_{50}$ ± S.E.M. (nM) |
| --- | --- |
| Rapamycin | 0.91 ± 0.36 |
| 2-pyridone | 12.39 ± 5.3 |
| 4-pyridone | 0.43 ± 0.20 |
| Example 1 | 1.70 ± 0.48 |
| Example 2 | 0.66 ± 0.19 |

The pharmacokinetic behaviors of Example 1 and Example 2 were characterized following a single 2.5 mg/kg intravenous dose in cynomolgus monkey (n=3 per group). Each compound was prepared as 2.5 mg/mL solution in a 20% ethanol:30% propylene glycol:2% cremophor EL:48% dextrose 5% in water vehicle. The 1 mL/kg intravenous dose was administered as a slow bolus (~1–2 minutes) in a saphenous vein of the monkeys. Blood samples were obtained from a femoral artery or vein of each animal prior to dosing and 0.1 (IV only), 0.25, 0.5, 1, 1.5, 2, 4, 6, 9, 12, 24, and 30 hours after dosing. The EDTA preserved samples were thoroughly mixed and extracted for subsequent analysis.

An aliquot of blood (1.0 mL) was hemolyzed with 20% methanol in water (0.5 ml) containing an internal standard. The hemolyzed samples were extracted with a mixture of ethyl acetate and hexane (1:1 (v/v), 6.0 mL). The organic layer was evaporated to dryness with a stream of nitrogen at room temperature. Samples were reconstituted in methanol:water (1:1, 150 μL). The tide compounds (50 μL injection) were separated from contaminants using reverse phase HPLC with UV detection. Samples were kept cool (4° C.) through the run. All samples from each study were analyzed as a single batch on the HPLC.

Area under the curve (AUC) measurements of Example 1, Example 2 and the internal standard were determined using the Sciex MacQuanTm software. Calibration curves were derived from peak area ratio (parent drugrmternal standard) of the spiked blood standards using least squares linear regression of the ratio versus the theoretical concentration. The methods were linear for both compounds over the range of the standard curve (correlation >0.99) with an estimated quantitation limit of 0.1 ng/mL. The maximum blood concentration ($C_{MAX}$) and the time to reach the maximum blood concentration ($T_{MAX}$) were read directly from the observed blood concentration-time data. The blood concentration data were submitted to multi-exponential curve fitting using CSTRIP to obtain estimates of pharmacokinetic parameters. The estimated parameters were further defined using NONLIN84. The area under the blood concentration-time curve from 0 to t hours (Gast measurable blood concentration time point) after dosing ($AUC_{0-t}$) was calculated using the linear trapeziodal rule for the blood-time profiles. The residual area extrapolated to infinity, determined as the final measured blood concentration ($C_t$ divided by the terminal elimination rate constant ($\beta$), and added to $AUC_{0-t}$ to produce the total area under the curve ($AUC_{0-t}$).

As shown in FIG. 1 and Table 2, both Example 1 and Example 2 had a suprisingly substantially shorter terminal elimination half-life ($t_{1/2}$) when compared to rapamycin. Thus, only the compounds of the invention provide both sufficient efficacy (Table 1) and a shorter terminal half-life (Table 2).

TABLE 2

| Compound | AUC µg · hr/mL | $t_{1/2}$ (hours) |
|---|---|---|
| Rapamycin | 6.87 | 16.7 |
| 2-pyridone | 2.55 | 2.8 |
| 4-pyridone | 5.59 | 13.3 |
| Example 1 | 2.35 | 5.0 |
| Example 2 | 2.38 | 6.9 |

Methods of Treatment

The compounds of the invention, including but not limited to those specified in the examples, possess immunomodulatory activity in mammals (especially humans). As immunosuppressants, the compounds of the present invention are useful for the treatment and prevention of immune-mediated diseases such as the resistance by transplantation of organs or tissue such as heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimnmune diseases such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like. Further uses include the treatment and prophylaxis of inflammatory and hyperproliferative skin diseases and cutaneous manifestations of imrunologically-mediated illnesses, such as psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of this invention. Inflammation of mucosa and blood vessels such as gastric ulcers, vascular damage caused by ischemnic diseases and thrombosis. Moreover, hyperproliferative vascular diseases such as intimal smooth muscle cell hyperplasia, restenosis and vascular occlusion, particularly following biologically- or mechanically-mediated vascular injury, could be treated or prevented by the compounds of the invention. Other treatable conditions include but are not limited to ischemic bowel diseases, inflammatory bowel diseases, necrotizing enterocolitis, intestinal inflammations/ allergies such as Coeliac diseases, proctitis, eosinophilic gastroenteritis, mastocytosis, Crohn's disease and ulcerative colitis; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemnia-reperfusion injury of organs (such as heart, liver, kidney and digestive tract) which occurs upon preservation, transplantation or ischemic disease (for example, thrombosis and cardiac infarction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-$C_4$ release; Behcet's disease such as intestinal-, vasculo- or neuro-Behcet's disease, and also Behcet's which affects the oral cavity, skin, eye, vulva, articulation, epididyris, lung, kidney and so on. Furthermore, the compounds of the invention are useful for the treatment and prevention of hepatic disease such as immunogenic diseases (for example, chronic autoimmune liver diseases such as autoimmune hepatitis, primary biliary cirrhosis and sclerosing cholangitis), partial liver resection, acute liver necrosis (e.g. necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, cytomegalovirus infection, particularly HCMV infection, anti-inflammatory activity, sclerosing and fibrotic diseases such as nephrosis, scleroderma, pulmonary fibrosis, arteriosclerosis, congestive heart failure, ventricular hypertrophy, post-surgical adhesions and scarring, stroke, myocardial infarction and injury associated with ischemia and reperfusion, and the like.

Additionally, compounds of the invention possess FK-506 antagonistic properties. The compounds of the present invention may thus be used in the treatment of immunodepression or a disorder involving immunodepression. Examples of disorders involving immnunodepression include AIDS, cancer, fungal infections, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2- cyclohexyl-1-methylvinyl)-13, 19,21,27-tetramethyl-11,28-dioxa-4-azatricyclo[22.3.1.0$^{4,9}$] octacos-18-ene such as FK-506 or rapamycin. The overdosing of such medicants by patients is quite common upon their realizing that they have forgotten to take their medication at the prescribed time and can lead to serious side effects.

The ability of the compounds of the invention to treat proliferative diseases can be demonstrated according to the methods described in Bunchman E T and C A Brookshire, Transplantation Proceed. 23 967–968 (1991); Yamagishi, et al., Biochem. Biophys. Res. Comm. 191 840–846 (1993); and Shichiri, et al., J. Clin. Invest 87 1867–1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels. In addition, these compounds antagonize cellular responses to several growth factors, and therefore possess antiangiogenic properties, making them useful agents to control or reverse the growth of certain tumors, as well as fibrotic diseases of the lung, liver, and kidney.

Aqueous liquid compositions of the present invention are particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.01 to about 10 mg/kg/day. For purposes of oral administration, more preferable doses may be in the range of from about 0.001 to about 3 mg/kg/day. If desired, the effective daily dose may be divided into multiple doses for purposes of administration; consequently, single dose compositions may contain such amounts or submultiples thereof to make up the daily dose. Topical adminstration may involve doses ranging from 0.001 to 3% mg/kg/day, depending on the site of application.

Pharmaceutical Compositions

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. The phrase "pharmaceutically acceptable carrier" means a non-toxic solid, semi-solid or liquid filler, diluent, encapsulating material or formulation auxiliary of any type. The term "parenteral," as used herein, refers to modes of administration which include intravenous, intramuscular, intraperitoneal, intrasternal, subcutaneous and intrarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and to poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable imedium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. Compositions for topical use on the skin also include oinments, creams, lotions, and gels.

Alternatively, the composition may be pressurized and contain a compressed gas, such as nitrogen or a liquified gas propellant. The liquified propellant medium and indeed the total composition is preferably such that the active ingredient does not dissolve therein to any substantial extent The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as automimmue diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroidiretina and sclera The pharmaceutically acceptable ophthalmic vehicle may, for example, be an ointment, vegetable oil or an encapsulating material.

Compositions for rectal or vaginal administration are preferably suppositories or retention enemas which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lameilar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Compounds of the present invention may also be coadministered with one or more immunosuppressant agents. The immunosuppressant agents within the scope of this invention include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A method for inhibiting restenosis in a mammal in need of said treatment, comprising administering to the mammal a therapeutically effective amount of a compound having the formula:

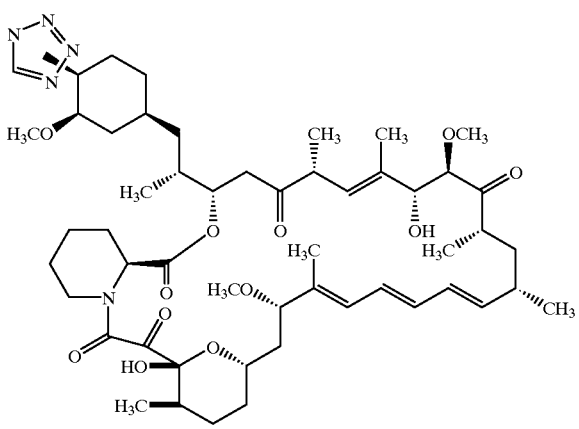

or a pharmaceutically acceptable salt or prodrug thereof.

2. A method for inhibiting restenosis in a mammal in need of said treatment, said method comprising administering to the mammal a therapeutically effective amount of a pharmaceutical composition, said pharmaceutical composition comprising a compound of a formula:

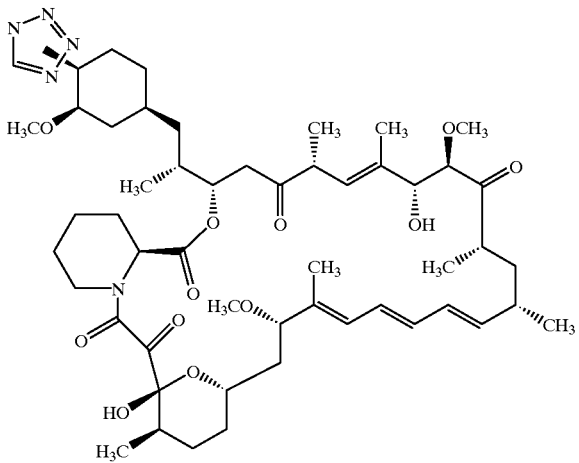

or a pharmaceutically acceptable salt or prodrug thereof.

3. The method for inhibiting restenosis in a mammal in accordance with claim 2 wherein said pharmaceutical composition further comprises a pharmaceutically acceptable carrier.

4. The method for inhibiting restenosis in a mammal in accordance with claim 2 wherein said pharmaceutical composition further comprises a pharmaceutically acceptable excipient.

5. The method for inhibiting restenosis in a mammal in accordance with claim 2 wherein said pharmaceutical composition further comprises a biodegradable polymer.

6. A method for preventing restenosis in a mammal in need of said, prevention, said method comprising administering to the mammal a therapeutically effective amount of a pharmaceutical composition, said pharmaceutical composition comprising a compound of a formula:

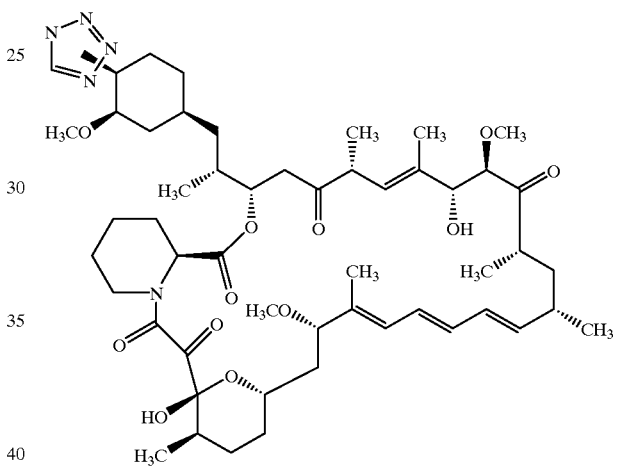

or a pharmaceutically acceptable salt or prodrug thereof.

7. The method for preventing restenosis in a mammal in accordance with claim 6 wherein said pharmaceutical composition further comprises a pharmaceutically acceptable carrier.

8. The method for preventing restenosis in a mammal in accordance with claim 6 wherein said pharmaceutical composition further comprises a pharmaceutically acceptable excipient.

9. The method for preventing restenosis in a mammal in accordance with claim 6 wherein said pharmaceutical composition further comprises a biodegradable polymer.

10. A method for treating restenosis in a mammal in need of said treatment, said method comprising administering to the mammal a therapeutically effective amount of a pharmaceutical composition, said pharmaceutical composition comprising a compound of a formula:

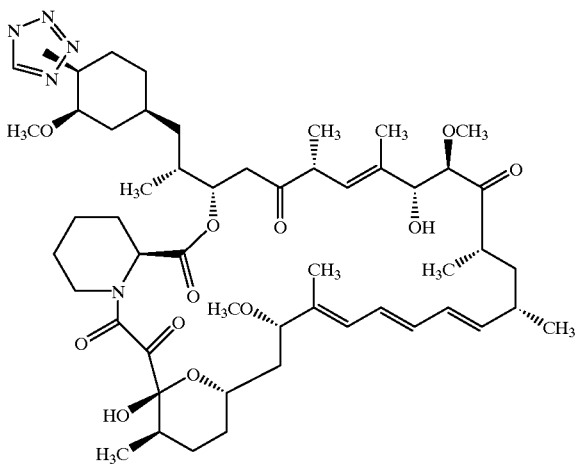

or a pharmaceutically acceptable salt or prodrug thereof.

11. The method for treating restenosis in a mammal in accordance with claim 10 wherein said pharmaceutical composition further comprises a pharmaceutically acceptable carrier.

12. The method for treating restenosis in a mammal in accordance with claim 10 wherein said pharmaceutical composition further comprises a pharmaceutically acceptable excipient.

13. The method for treating restenosis in a mammal in accordance with claim 10 wherein said pharmaceutical composition further comprises a biodegradable polymer.

14. A method for treating a hyperproliferative disease in a mammal in need of said treatment, wherein said hyperproliferative disease is selected from the group consisting of vascular hyperproliferative diseases and skin hyperproliferative diseases, said method comprising administering to the mainnnal a therapeutically effective amount of a pharmaceutical composition, said pharmaceutical composition comprising a compound of a formula;

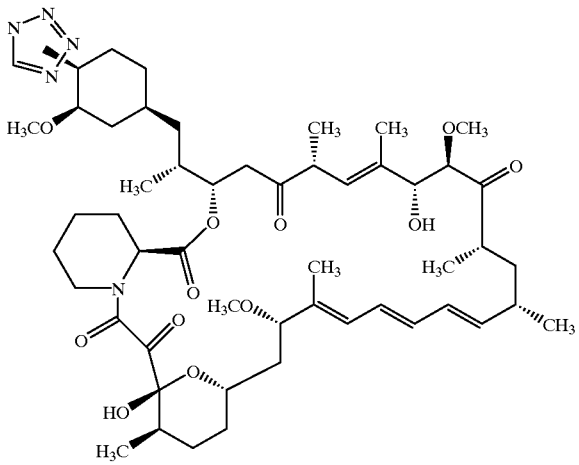

or a pharmaceutically acceptable salt or prodrug thereof.

15. The method for treating a hyperproliferative disease in a mammal in accordance with claim 14 wherein said pharmaceutical composition further comprises a pharmaceutically acceptable carrier.

16. The method for treating a hyperproliferative disease in a mammal in accordance with claim 14 wherein said pharmaceutical composition further comprises a pharmaceutically acceptable excipient.

17. The method for treating a hyperproliferative disease in a mammal in accordance with claim 14 wherein said pharmaceutical composition further comprises a biodegradable polymer.

18. A method for preventing a hyperproliferative disease in a mamnual in need of said prevention, wherein said hyperproliferative disease is selected from the group consisting of vascular hyperproliferative diseases and skin hyperproliferative diseases, said method comprising administering to the mammal a therapeutically effective amount of a pharmaceutical composition, said pharmaceutical composition comprising a compound of a formula:

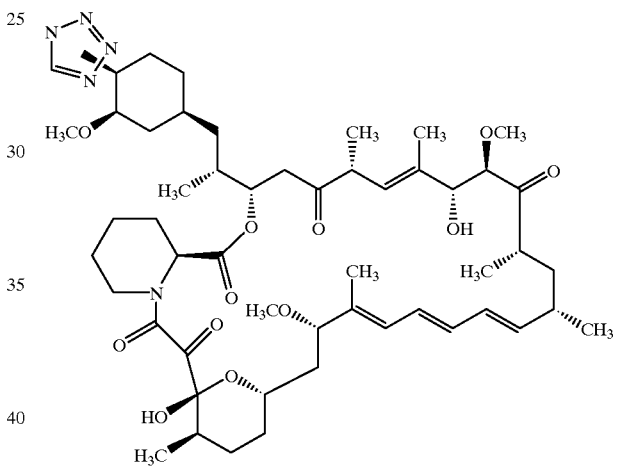

or a pharmaceutically acceptable salt or prodrug thereof.

19. A method for preventing a hyperproliferative disease in a mammal in accordance with claim 18 wherein said pharmaceutical composition further comprises a pharmaceutically acceptable carrier.

20. A method for preventing a hyperproliferative disease in a mammal in accordance with claim 18 wherein said pharmaceutical composition further comprises a pharmaceutically acceptable excipient.

21. The method preventing a hyperproliferative disease in a mammal in accordance with claim 18 wherein said pharmaceutical composition further comprises a biodegradable polymer.

* * * * *

UNITED STATES PATENT AND TRADEMARK OFFICE
CERTIFICATE OF CORRECTION

PATENT NO. : 6,329,386 B1
DATED : December 11, 2001
INVENTOR(S) : Karl W. Mollison It is certified that error appears in the above-identified patent and that said Letters Patent is hereby corrected as shown below:

<u>Column 17,</u>
Line 38, replace "mainnnal" with -- mammal --

Signed and Sealed this

Sixteenth Day of July, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.        : 6,329,386 B1                                            Page 1 of 10
APPLICATION NO. : 09/433001
DATED             : December 11, 2001
INVENTOR(S)      : Karl W. Mollison It is certified that error appears in the above-identified patent and that said Letters Patent is hereby corrected as shown below:

On the cover page, under item [57] "Abstract", delete:

" 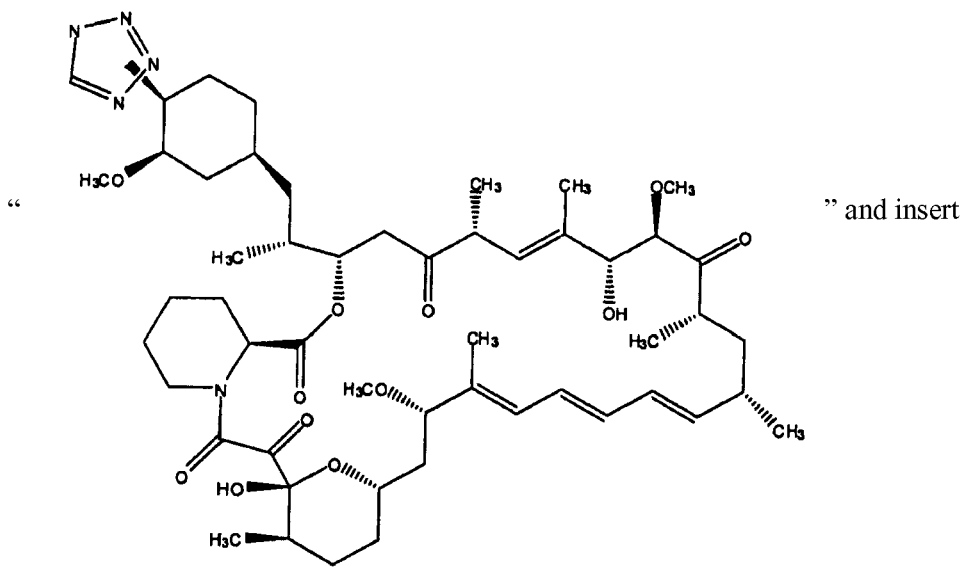 " and insert

-- 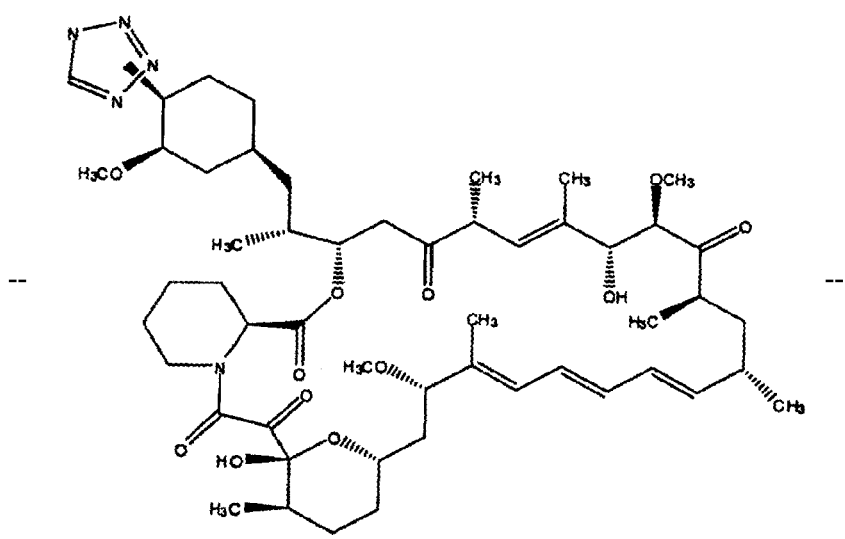 --

UNITED STATES PATENT AND TRADEMARK OFFICE
CERTIFICATE OF CORRECTION

PATENT NO. : 6,329,386 B1
APPLICATION NO. : 09/433001
DATED : December 11, 2001
INVENTOR(S) : Karl W. Mollison Page 2 of 10

It is certified that error appears in the above-identified patent and that said Letters Patent is hereby corrected as shown below:

At column 3, lines 31 – 49, delete:

" 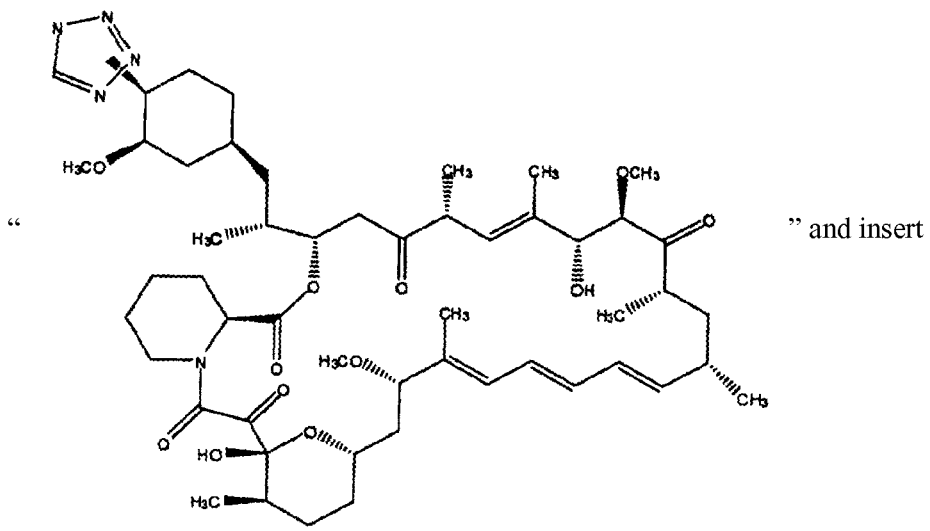 " and insert

-- 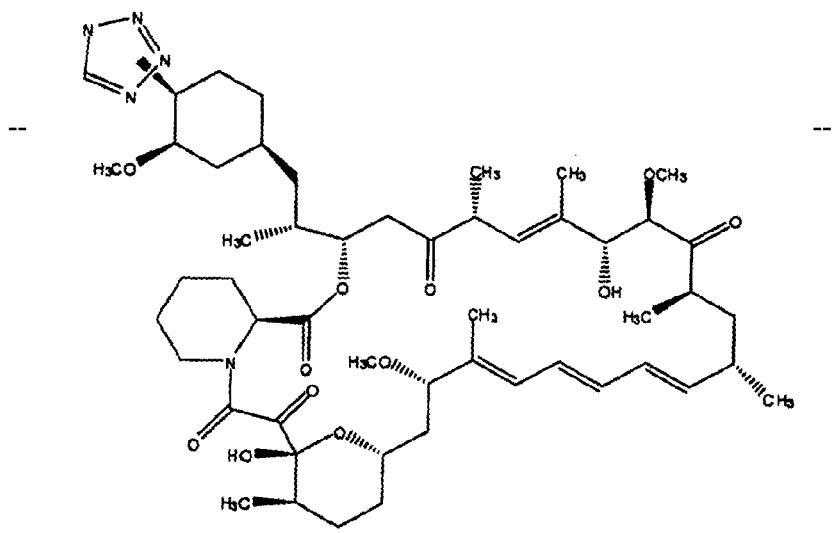 --

UNITED STATES PATENT AND TRADEMARK OFFICE
CERTIFICATE OF CORRECTION

PATENT NO. : 6,329,386 B1  
APPLICATION NO. : 09/433001  
DATED : December 11, 2001  
INVENTOR(S) : Karl W. Mollison Page 3 of 10

It is certified that error appears in the above-identified patent and that said Letters Patent is hereby corrected as shown below:

At column 4, lines 45 – 64, delete:

" 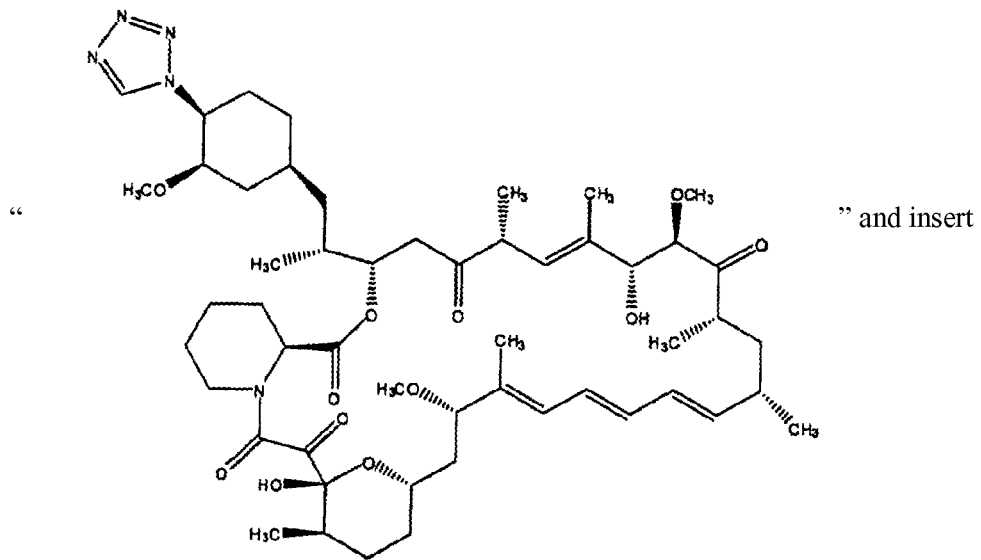 " and insert

-- 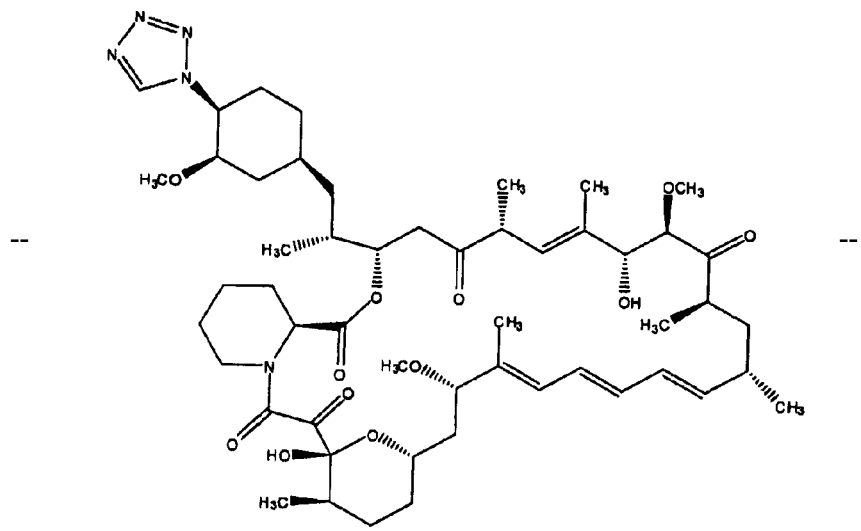 --

UNITED STATES PATENT AND TRADEMARK OFFICE
CERTIFICATE OF CORRECTION

PATENT NO.       : 6,329,386 B1
APPLICATION NO.  : 09/433001
DATED            : December 11, 2001
INVENTOR(S)      : Karl W. Mollison It is certified that error appears in the above-identified patent and that said Letters Patent is hereby corrected as shown below:

At column 5, lines 1 – 24, delete:

" 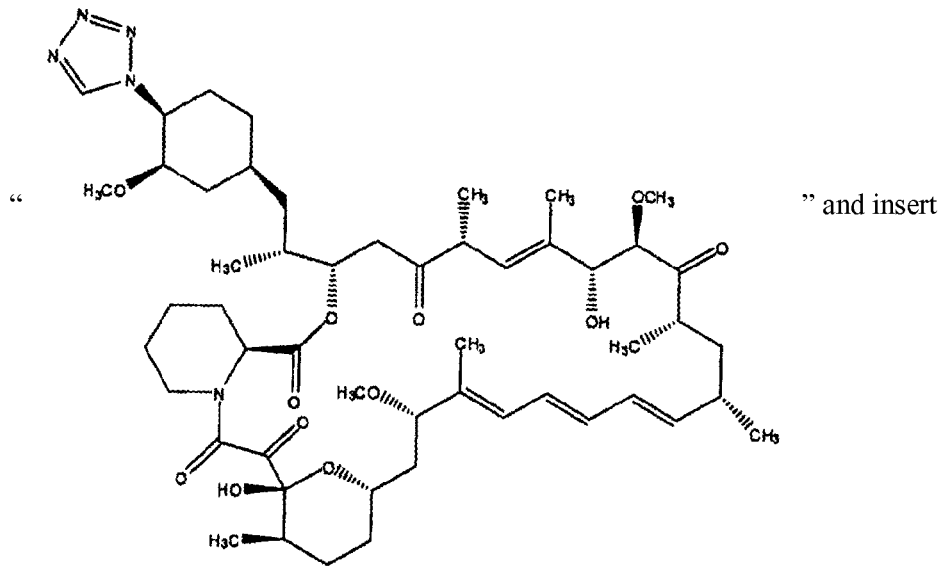 " and insert

-- 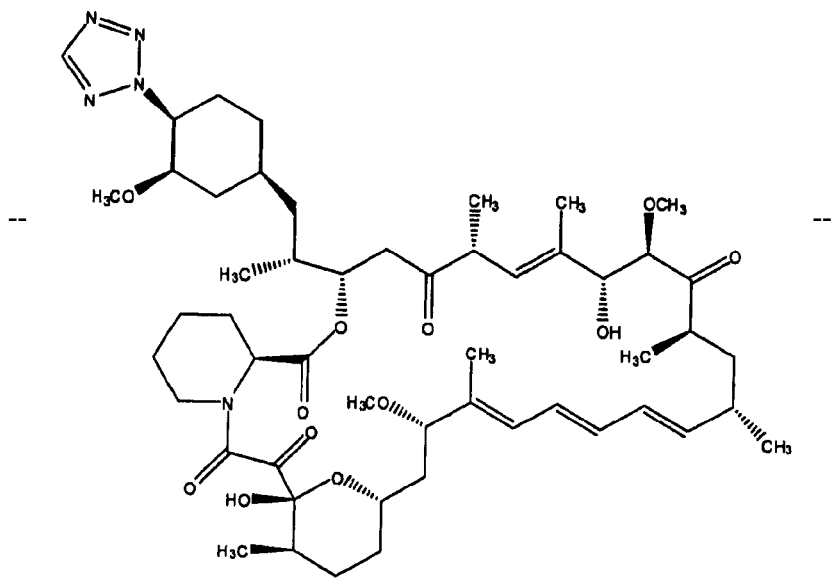 --

UNITED STATES PATENT AND TRADEMARK OFFICE
CERTIFICATE OF CORRECTION

PATENT NO. : 6,329,386 B1
APPLICATION NO. : 09/433001
DATED : December 11, 2001
INVENTOR(S) : Karl W. Mollison It is certified that error appears in the above-identified patent and that said Letters Patent is hereby corrected as shown below:

At column 15, line 15 delete the text beginning with "1. A method" to and ending with "or prodrug thereofs" at column 15, line 39 and insert the following claim:

--1. A method for inhibiting restenosis in a mammal in need of said treatment, comprising administering to the mammal a therapeutically effective amount of a compound having the formula:

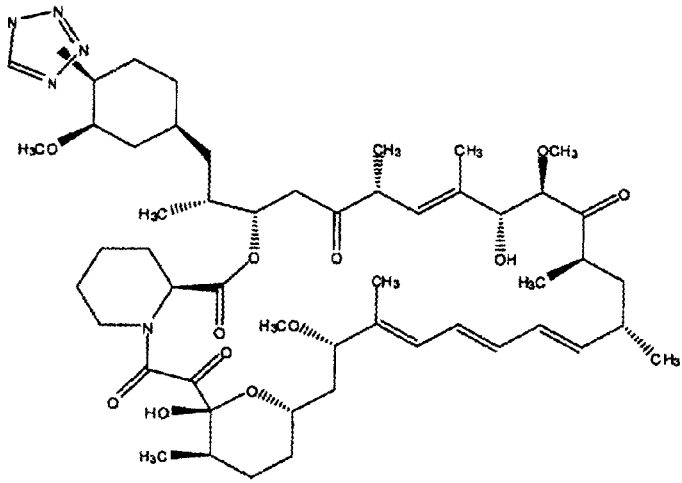

or a pharmaceutically acceptable salt or prodrug thereof.--

UNITED STATES PATENT AND TRADEMARK OFFICE
CERTIFICATE OF CORRECTION

PATENT NO. : 6,329,386 B1
APPLICATION NO. : 09/433001
DATED : December 11, 2001
INVENTOR(S) : Karl W. Mollison It is certified that error appears in the above-identified patent and that said Letters Patent is hereby corrected as shown below:

At column 15, lines 40 delete the text beginning with "2. A method" to and ending with "or prodrug thereof." at column 15, line 67 (claim 2), and insert the following claim:

--2. A method for inhibiting restenosis in a mammal in need of said treatment, said method comprising administering to the mammal a therapeutically effective amount of a pharmaceutical composition, said pharmaceutical composition comprising a compound of a formula:

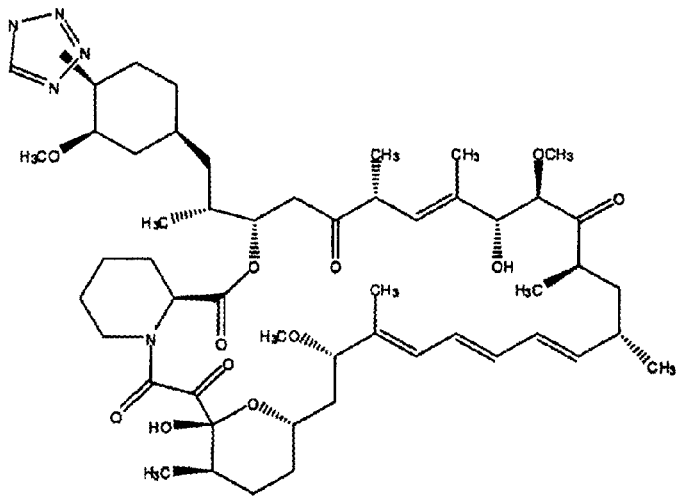

or a pharmaceutically acceptable salt or prodrug thereof.--

UNITED STATES PATENT AND TRADEMARK OFFICE
CERTIFICATE OF CORRECTION

PATENT NO.         : 6,329,386 B1
APPLICATION NO.    : 09/433001
DATED              : December 11, 2001
INVENTOR(S)        : Karl W. Mollison It is certified that error appears in the above-identified patent and that said Letters Patent is hereby corrected as shown below:

At column 16, lines 17 delete the text beginning with "6. A method" to and ending with "or prodrug thereof." at column 16, line 45, and insert the following claim:

--6. A method for preventing restenosis in a mammal in need of said prevention, said method comprising administering to the mammal a therapeutically effective amount of a pharmaceutical composition, said pharmaceutical composition comprising a compound of a formula:

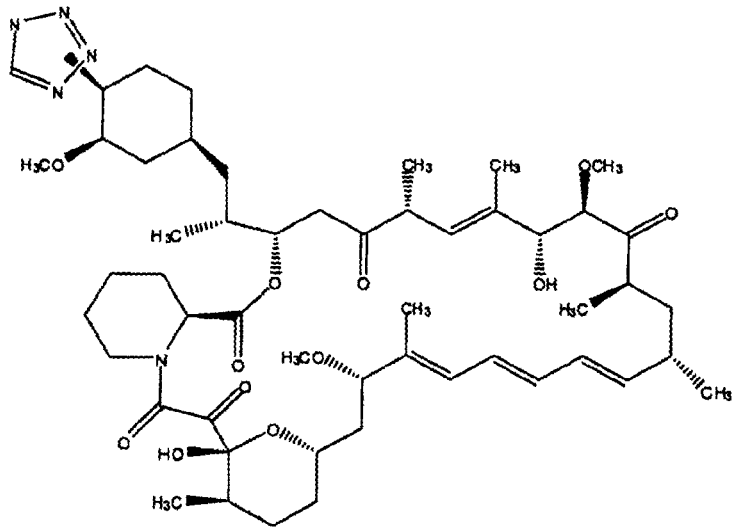

or a pharmaceutically acceptable salt or prodrug thereof.--

UNITED STATES PATENT AND TRADEMARK OFFICE
CERTIFICATE OF CORRECTION

PATENT NO. : 6,329,386 B1
APPLICATION NO. : 09/433001
DATED : December 11, 2001
INVENTOR(S) : Karl W. Mollison It is certified that error appears in the above-identified patent and that said Letters Patent is hereby corrected as shown below:

At column 16, lines 63, delete the text beginning with "10. A method" to and ending with "or prodrug thereof." at column 17, lines 21, and insert the following claim:

--10. A method for treating restenosis in a mammal in need of said treatment, said method comprising administering to the mammal a therapeutically effective amount of a pharmaceutical composition, said pharmaceutical composition comprising a compound of a formula:

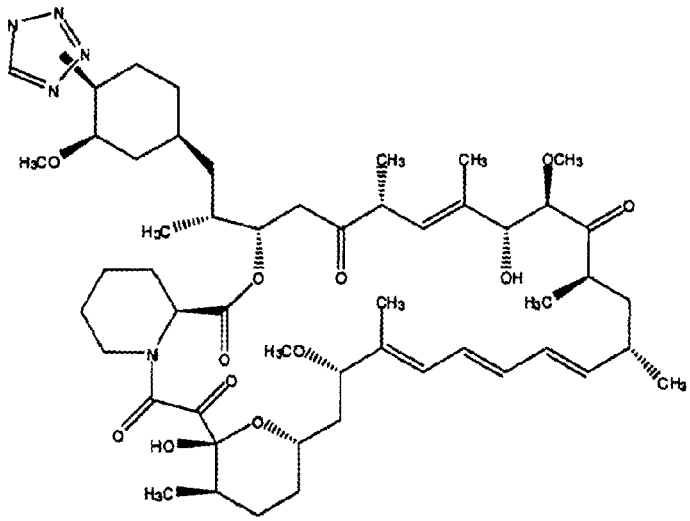

or a pharmaceutically acceptable salt or prodrug thereof.--

UNITED STATES PATENT AND TRADEMARK OFFICE
CERTIFICATE OF CORRECTION

| | |
|---|---|
| PATENT NO. | : 6,329,386 B1 |
| APPLICATION NO. | : 09/433001 |
| DATED | : December 11, 2001 |
| INVENTOR(S) | : Karl W. Mollison |

It is certified that error appears in the above-identified patent and that said Letters Patent is hereby corrected as shown below:

At column 17, lines 33, delete the text beginning with "14. A method," to and ending with "or prodrug thereof." at column 17, line 60, and insert the following claim:

--14. A method for treating a hyperproliferative disease in a mammal in need of said treatment, wherein said hyperproliferative disease is selected from the group consisting of vascular hyperproliferative diseases and skin hyperproliferative diseases, said method comprising administering to the mammal a therapeutically effective amount of a pharmaceutical composition, said pharmaceutical composition comprising a compound of a formula:

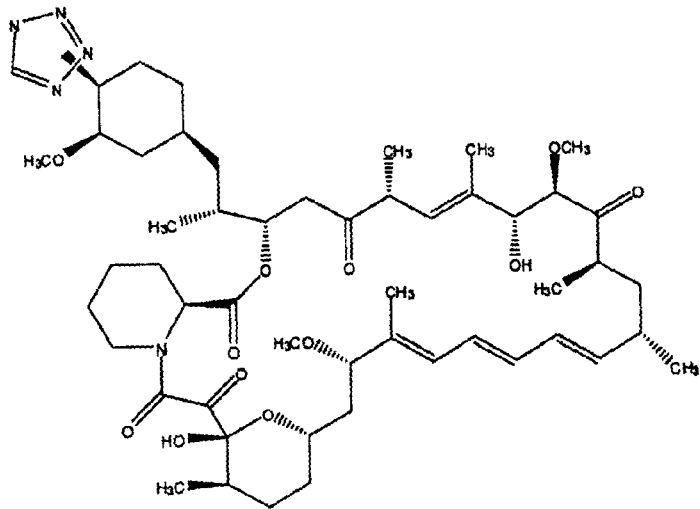

or a pharmaceutically acceptable salt or prodrug thereof.--

UNITED STATES PATENT AND TRADEMARK OFFICE
CERTIFICATE OF CORRECTION

PATENT NO. : 6,329,386 B1
APPLICATION NO. : 09/433001
DATED : December 11, 2001
INVENTOR(S) : Karl W. Mollison It is certified that error appears in the above-identified patent and that said Letters Patent is hereby corrected as shown below:

At column 18, lines 15, delete the text beginning with "18. A method" to and ending with "or prodrug thereof." at column 18, line 45, and insert the following claim 18:

--18. A method for preventing a hyperproliferative disease in a mammal in need of said prevention, wherein said hyperproliferative disease is selected from the group consisting of vascular hyperproliferative diseases and skin hyperproliferative diseases, said method comprising administering to the mammal a therapeutically effective amount of a pharmaceutical composition, said pharmaceutical composition comprising a compound of a formula:

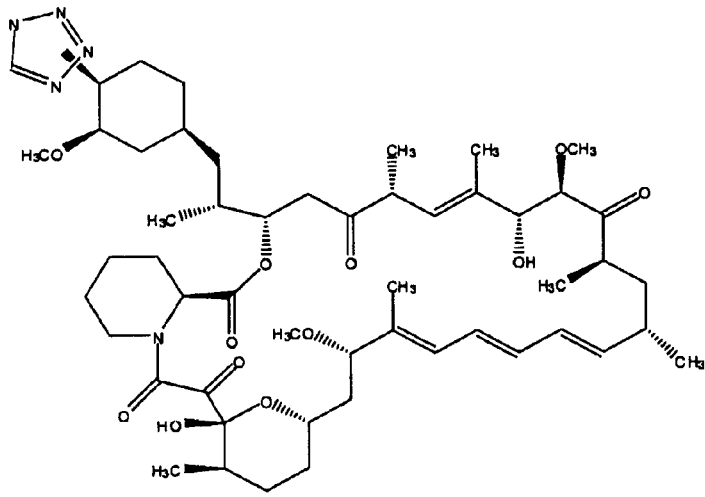

or a pharmaceutical acceptable salt or prodrug thereof.--

Signed and Sealed this

Tenth Day of February, 2009

JOHN DOLL
*Acting Director of the United States Patent and Trademark Office*